United States Patent [19]

Meyer

[11] Patent Number: 4,647,777
[45] Date of Patent: Mar. 3, 1987

[54] SELECTIVE GAS DETECTOR

[75] Inventor: Emilio Meyer, Pittsburgh, Pa.

[73] Assignee: Ametrek, Inc., New York, N.Y.

[21] Appl. No.: 740,186

[22] Filed: May 31, 1985

[51] Int. Cl.$^4$ ............................................. G01N 21/35
[52] U.S. Cl. ..................... 250/339; 250/338; 250/345; 250/347; 250/349; 250/353; 356/435; 356/437
[58] Field of Search ............... 250/338 GA, 353, 349, 250/344, 343, 339, 340, 347, 345; 356/435, 437

[56] References Cited

U.S. PATENT DOCUMENTS

| | | | |
|---|---|---|---|
| 2,703,844 | 3/1955 | Miller | 250/346 |
| 2,849,618 | 8/1958 | Smith | 250/339 |
| 3,364,351 | 1/1968 | Palmer et al. | 250/339 |
| 3,588,496 | 6/1971 | Snowman | 250/343 |
| 3,743,430 | 7/1973 | Riggs | 356/435 |
| 3,790,289 | 2/1974 | Schmidt | 356/434 |
| 3,838,925 | 10/1974 | Marks | 356/438 |
| 3,849,005 | 11/1974 | Girard et al. | 356/438 |
| 3,872,315 | 3/1975 | Boll | 250/575 |
| 3,916,195 | 10/1975 | Burch et al. | 250/345 |
| 3,935,463 | 1/1976 | Jacobsen | 250/373 |
| 3,954,342 | 5/1976 | Boeke | 356/435 |
| 3,970,387 | 7/1976 | Faulhaber et al. | 356/51 |
| 3,998,384 | 12/1976 | Martin et al. | 236/87 |
| 4,126,396 | 11/1978 | Hartmann et al. | 356/434 |
| 4,152,075 | 5/1979 | Rellstab et al. | 356/435 |
| 4,171,909 | 10/1979 | Kramer et al. | 356/73 |
| 4,180,734 | 12/1979 | Gedeon | 250/345 |
| 4,205,913 | 6/1980 | Ehrfeld et al. | 356/72 |
| 4,306,152 | 12/1981 | Ross et al. | 250/343 |

FOREIGN PATENT DOCUMENTS 2254234 7/1975 France .................... 417/151

Primary Examiner—Janice A. Howell
Assistant Examiner—Constantine Hannaher
Attorney, Agent, or Firm—Amster, Rothstein & Ebenstein

[57] ABSTRACT

A selective infra-red detector is used to determine the amount of a selected gas present in a gas sample. A beam of infra-red energy is passed through a gas sample and into the selective infra-red detector. An outer annular portion of the beam is reflected from a paraboloidal mirror onto a first focal point, while an inner annular portion of the beam passes through a chamber containing a fluid which will absorb the spectral wavelengths of the selected gas and is reflected by a spherical mirror onto a second focal point. Separate infra-red energy detectors are positioned near the first and second focal points to measure the infra-red energy. The difference or ratio between the infra-red energy measured by each infra-red energy detector is a measure of the amount of selected gas present in the gas sample.

3 Claims, 6 Drawing Figures

SELECTIVE GAS DETECTOR

This invention relates to a method and apparatus for detecting and measuring the amount of a selected gas in a gas sample.

Measurement of the presence and amount of a selected gas in a gas sample requires the use of sophisticated and accurate detecting and measuring devices since often, the selected gas is present in only relatively minute quantities. In the past, infra-red energy systems have been used to accomplish this task. In such a system, infra-red energy is transmitted through a gas sample and detected. One type of infra-red energy system utilized two separate infra-red energy sources and two separate infra-red energy detectors. Such systems suffered from a number of problems, including differences in the aging rate of the infra-red energy sources, difficulty in maintaining a small temperature gradient between the infra-red energy detectors and non-uniformity of the infra-red energy transmitted in separate beams by the infra-red energy sources. All of these problems resulted in deficiencies in the accuracy of the resultant measurements. Systems using a single infra-red energy source are also known. Those systems generally require rotating structures which alternately cause the single beam of infra-red energy to fall on separate infra-red energy detectors, or use beam splitters for splitting the beam of infra-red energy into separate components, which separate components are detected by separate infra-red energy detectors. Further, gas detectors must often be used in a hostile environment subject to varying environmental conditions. Detectors which, for example, use rotating structures are subject to damage when used in those environments.

In prior infra-red energy gas detecting systems, one beam of infra-red energy is directed through a filter or other apparatus which absorbs the wavelengths of the selected gas prior to being detected by the first infra-red energy detector and the other beam of infra-red energy is directed to the second infra-red energy detector without passing through a filter. The difference between the amount of infra-red energy detected by the first and second infra-red energy detectors represents the amount of selected gas in the sample. These systems, however, do not focus the portions of the beam to concentrate the infra-red energy on, or adjacent to, the infra-red energy detectors. Since the amount of the selected gas in the gas sample is usually small, and since often the selected gas does not absorb much of the energy of the infra-red energy beam, these prior gas detecting systems do not provide as accurate a measurement of the selected gas as is desired.

One of the current and continuing environmental problems, which must be addressed, is the monitoring and regulation of gasses, known as stack gasses, which contain pollutants and which evolve from gas stacks or chimneys. Environmental laws require that various pollutants be kept below specified and usually minute quantities. Gas detectors are used to both monitor the amount of the pollutant gas present in the stack gas and to provide signals to directly control the furnace producing the gasses. Such detectors must be capable of precise measurements of minute amounts of the selected gas and be capable of being placed in or closely adjacent to the stack or chimney. Those gas detectors must be rugged in construction and capable of performing the detection or measuring of the selected gas for extended periods of time. In general, infra-red gas detectors to monitor and measure stack gas use an infra-red energy source mounted on one side of the chimney and an infra-red energy detector mounted on the opposite side of the chimney, resulting in a relatively large separation of the infra-red energy source and infra-red energy detector creating further problems in obtaining accurate measurements.

Accordingly, it is an object of the invention to improve upon the prior infra-red energy gas detection systems and, in particular, to provide an improved infra-red energy gas detection system which is capable of detecting and measuring minute quantities of a selected gas in a gas sample. More specifically, it is an object of the invention to provide an improved infra-red energy detector for use in a system which monitors and measures small amounts of a selected gas in a gas sample.

Another object of the invention is to provide an infra-red gas detection and monitoring system which can monitor and detect selected pollutants present in stack gas.

Still further, it is an object of the invention to provide a system for use in monitoring stack gas which can be mounted closely adjacent to the chimney, is rugged in construction, and is capable of providing accurate measurement of a minute quantity of a selected gas present in the stack gas.

Still further, it is an object of this invention to provide a gas monitoring detecting system which can measure the concentration of potentially dangerous pollutants in stack gas and can be used to control the efficiency with which fuel is burned in a furnace.

More specifically, the invention is directed to a method and apparatus for monitoring and detecting a selected gas in a gas sample and to the detector used in such system. The overall apparatus includes a source of infra-red energy and an infra-red energy detector. The detector includes a housing having an inlet opening for receiving a beam of infra-red energy eminating from the source of infra-red energy, first focusing means for focusing a first portion of the beam of infra-red energy on a first focal point and second focusing means for focusing a second portion of the beam of infra-red energy on a second focal point. Means are provided to absorb certain of the spectral wavelengths of the second portion of the beam of infra-red energy, the wavelengths absorbed being dependent upon the gas to be detected. Infra-red energy detecting means are positioned proximate the first and second focal points to detect the amount of infra-red energy focused at those points and provide an indication of the amount of selected gas in the gas sample.

The method for detecting a selected gas, according to the present invention includes passing a beam of infra-red energy through a gas sample and causing a first portion of the beam of infra-red energy to be focused onto a first focal point and a second portion of the beam of infra-red energy to be focused onto a second focal point after certain of the spectral wavelengths of the second portion of the beam of infra-red energy are absorbed. The method further contemplates measuring the energy of the first and second portions of the beam of infra-red energy at the respective focal points to determine the presence and amount of the selected gas.

In a particular and preferred embodiment of the invention, a reflective system is used to focus the beam of infra-red energy. Specifically, the first focusing means includes a paraboloidal mirror mounted within a first mirror carrier and movable within a first portion of a housing and the second focusing means includes a spherical mirror mounted within a second mirror carrier and movable within a second portion of the housing. The use of mirrors to focus the beam of infra-red energy provides a sharper focus of the beam of infra-red energy at the respective focal points and a significant improvement over the use of lenses, which could also perform that function. However, the use of lenses can cause optical problems in the system. First, since the refractive index of the lens changes with wavelength of the incident beam of infra-red energy, and since that beam of infra-red energy contains a band of wavelengths, the beam of infra-red energy will not be focused down to as sharp an image as possible. Thus, the infra-red energy beam will not be as concentrated as possible at the focal point resulting in a loss of accuracy. Second, to pass the longer wavelengths of the infra-red beam requires the use of materials which are expensive or have other undesirable properties. These problems are overcome by the use of mirrors to focus the beam of infra-red energy. It is, of course, understood that the use of various types of mirrors can be used, however, a paraboloidal mirror is very effective in concentrating the infra-red energy at the focal point.

Ideally, for maximum accuracy, the temperature gradient between the two infra-red energy detectors should be zero. One of the problems with prior infra-red gas detectors was the difficulty in maintaining the temperature gradient between the two energy detectors as small as possible. In accordance with this invention, the first and second infra-red energy detectors are positioned in the housing relatively near each other and are mounted on a common heat sink such that the temperature gradient betweeen them is minimized or eliminated.

Further, in accordance with another feature of the invention, the second mirror carrier contains a material which absorbs the spectral wavelengths corresponding to the selected gas to be detected. This material is positioned forward of the spherical mirror so that the second portion of the infra-red energy beam passes through the absorption material twice before being focused at the second focal point, thereby increasing the amount of infra-red energy absorbed at that wavelength. In addition, according to the invention, both mirror carriers are movable in the housing relative to the infrared energy detectors so that the focal points of the first portion of the beam and the second portion of the beam may be independently adjusted to provide an optically balanced system.

These and other features and advantages of the invention will become more understandable in light of the following description taken in conjunction with the drawings, in which.

Figure 1:
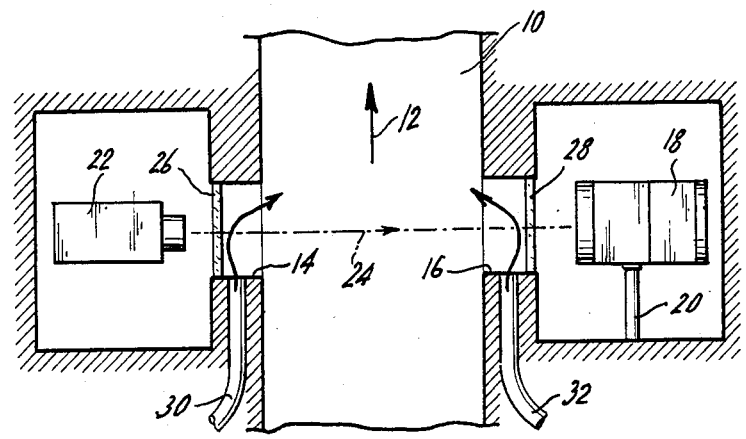
FIG. 1 is a diagramatic representation of a system for detecting and measuring selected gas in a gas stack sample using the selective infra-red detector of the invention.

Referring now to FIG. 1, there is illustrated a specific arrangement for using the selective infra-red gas detector of the invention to monitor and measure the carbon monoxide (CO) content of stack gas one of the applications for the gas detector of the invention. It is understood that the gas detector of the invention has many applications and the illustrated use does not narrow the intended scope of the invention. In FIG. 1, chimney 10 has stack gas flowing therethrough, as indicated by arrow 12, and a pair of side openings 14 and 16 formed therein. A selective infra-red detector 18, constructed in accordance with the invention, is suitably mounted on post 20 and aligned with opening 16 on one side of chimney 10. A source of infra-red energy 22 is suitably mounted on the opposite side of chimney 10 aligned with opening 14 and generates a collimated beam of infra-red energy 24 which passes through window 26, through stack gas 12, window 28 and enters detector 18. Suitable air purge passageways 30 and 32 are provided to permit circulation of purge gas past windows 26 and 28 to remove particulates which can become deposited on windows 26 and 28, respectively. With this arrangement, as described in more detail below, the amount of CO in the stack gas can be measured.

Figure 2:
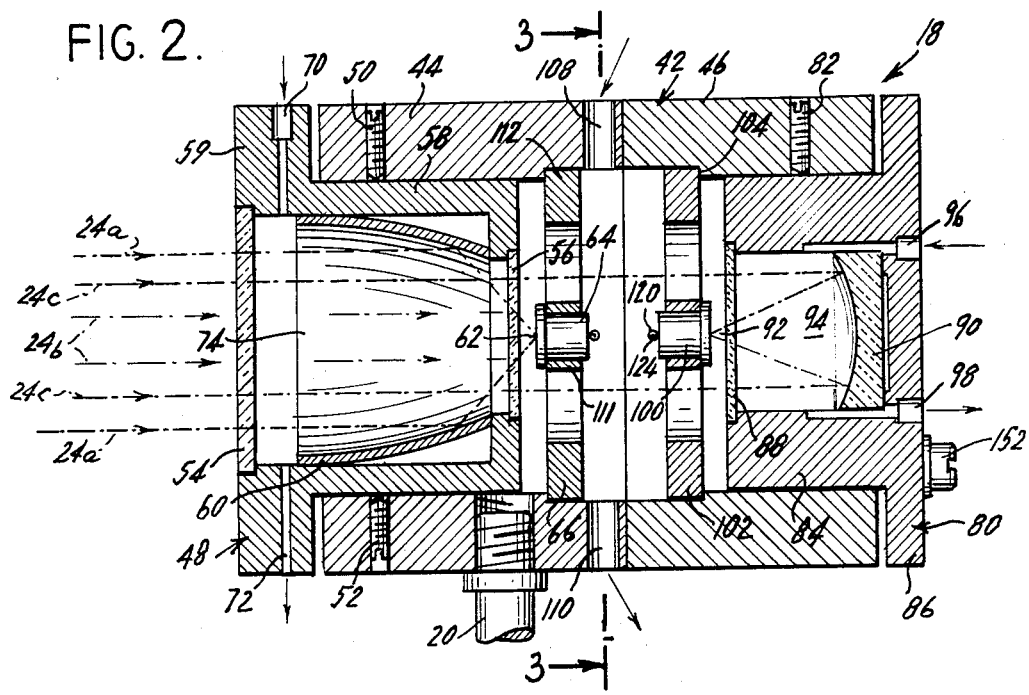
FIG. 2 is a vertical cross-sectional view of the selective infra-red detector of the invention.

Referring to FIG. 2, gas detector 18 includes housing 42 made, for example, of aluminum or other suitable material, having a front portion 44 and rear portion 46. First mirror carrier 48 is slidably mounted in the inner bore of first portion 44 of housing 42 and held in a fixed position by set screws 50, 52. A transparent plate 54 seals the forward end of first mirror carrier 48 and the rearward end of first mirror carrier 48 is sealed by an infra-red filter 56. First mirror carrier 48 includes an inner cylindrical portion 58 which is received within the bore of housing 42 and an outer annular flange portion 59 which is used to mount first mirror carrier 48 to housing 42, as described below.

A paraboloidal mirror, generally designated by reference number 60, is secured to the inner surface of first mirror carrier 48 and positioned to focus a portion of the beam of infra-red energy 24a at a first focal point 62, as described in detail below. Measurement infra-red detector 64, preferably a thermopile, is mounted in a first detector carrier 66, preferably made of aluminum, secured against shoulder 68 in the first portion 44 of housing 42 and positioned with the active portion thereof approximate to first focal point 62. First mirror carrier 48 also includes inlet port 70 and outlet port 72 which permits calibration gas to be introduced into and purged from the sealed chamber 74 formed between transparent plate 54 and infra-red filter 56, as generally indicated by the arrows.

A second mirror carrier 80, slidably mounted in rear portion 46 of housing 42 and held in a fixed position by set screw 82, includes an inner cylindrical portion 84 received within the bore of rear portion 46 of housing 42 and an annular flange portion 86 which is used to mount second mirror carrier 80 to housing 42 as described below. Transparent plate 88 seals the forward end of second mirror carrier 80. Spherical mirror 90 is mounted in the rear of second mirror carrier 80 and focuses a portion of the infra-red beam 24c onto a second focal point 92. Sealed chamber 94, formed in second mirror carrier 80, between transparent plate 88 and spherical mirror 90, is filled with a fluid which will absorb a portion of the spectrum of infra-red radiation in infra-red beam 24 corresponding to the wavelength of the selected gas to be monitored and measured. Inlet port 96 and outlet port 98 permit the infra-red absorbing fluid to be inserted into chamber 94 and to be purged therefrom and permit different infra-red absorbing fluids to be inserted into chamber 94, such that the gas detector of the invention can be used in connection with monitoring and measuring different gasses. Ports 96 and 98 are, of course, sealed after chamber 94 is filled. Reference infra-red detector 100, preferably a thermopile, is mounted in second detector carrier 102, preferably made of aluminum, secured against shoulder 104 in the second portion 46 of housing 42 and positioned with its active portion approximate second focal point 92. Infra-red energy detectors 62 and 100 are thus positioned proximate one another and on a common heat sink consisting of detector carriers 66, 102 and housing 42 to maintain detectors 62 and 100 at or near the same temperature. Finally, ports 108, 110 permit gas to be introduced into housing 42, as indicated by the arrows, between infra-red filter 56 and transparent plate 88 to purge that area of contaminants, if necessary.

Parabolic mirror 60 serves as a beam splitter in that the outer annular portion 24a of the infra-red energy beam 24 strikes and is reflected from, mirror 60 to first focal point 62. The central portion 24b of the beam of infra-red energy having a diameter equal to the diameter of measurement detector 64, strikes the surface of measurement detector 64. An intermediate annular portion of the beam of infra-red energy 24, designated by reference numeral 24c, passes through the circular opening in the far end of paraboloidal mirror 60 and also passes measurement detector 64 and enters fluid filled chamber 94 of second mirror carrier 80. This intermediate annular portion 24c of the beam of infra-red energy does not strike mirror 60, nor does it strike detector 64. The intermediate annular portion 24c of the beam of infra-red energy travels through the fluid in chamber 94, strikes spherical mirror 90, as reflected from spherical mirror back through the fluid in chamber 94 to second focal point 92. By measuring the difference between the energy incident to measurement detector 64 and reference detector 100, the presence and amount of selected gas on the gas stack can be measured. When using thermistor sensors this measurement can be carried out, for example, using a conventional wheatstone bridge in which the measurement detector 68 and reference detector 100 form two arms of the bridge, as would be well known in the art. In constructing detector 18, it is preferable that the amount of infra-red radiation reflected to focal points 62 and 92 be approximately the same. To this end, the cross-sectional area of the inlet end of mirror 60 is preferably approximately equal to twice the cross-sectional area of the outlet end of mirror 60. Infra-red filter 56 and transparent plate 88 act as bandpass filters to remove spectral wavelengths of energy except in a band of wavelengths of interest. While not required they are preferred in order to increase measurement accuracy. They are made of any suitable material as is well known in the art.

Prior to installing gas detector 18 for use in detecting stack gasses (or other applications for gas detector 18), two balancing procedures are required. The first procedure requires that the beam of infra-red energy be totally blocked from entering the detector 18, for example, by use of a suitable shutter in front of transparent plate 54. When no infra-red energy is present, the wheatstone bridge is balanced. When the shutter is removed, infra-red energy is transmitted directly to detector 18 and focused at the first and second focal points. If the wheatstone bridge becomes unbalanced, either or both of mirror carriers 48, 80 are moved axially relative to infra-red energy detectors 64, 100 to rebalance the bridge. The first electrical procedure is needed only when thermistor sensors are used. The second procedure is an optical balancing procedure. To carry this out, chamber 74 is first purged of gas by passing an appropriate purging gas therethrough by way of ports 70 and 72. Chamber 74 is then filled with 100% of the gas it is desired to detect. In the example, this gas is CO. Thus, both chambers 74 and 94 are filled with fluids which will absorb the spectral wavelengths of CO from a beam of infra-red energy. A beam of infra-red energy is then transmitted through transparent plate 54 and focused at focal points 62 and 92. Since all spectral wavelengths corresponding to CO should have been removed from the beam, the infra-red radiation detected by both detectors 64 and 100 should be equal and the bridge should be balanced. If the bridge is not balanced, one or both mirror carriers 48, 80 are moved axially until the bridge is balanced. Thus, chamber 74 functions as a test cell, considerably simplifying the balancing procedure from prior procedures requiring the use of separate test cells.

The optical balance controls the amount of energy transferred to each of the infra-red energy detectors 64, 100 from the portions of the infra-red energy beam 24. When optical balance is obtained, only a variation in the concentration of the gas in the gas sample, for example, CO in the stack gas, alters this balanced condition. The amount of this unbalance, which is read on an appropriate meter, provides a measurement of the concentration of the selected gas in the gas sample. Alternatively, a signal representing the unbalanced condition can be fed back to the furnace control system to affect the combustion of gasses in the furnace to reduce pollutants. With the detector of this invention, variations in the infra-red energy emitted by the infra-red energy source, or a variation in the transmission properties of the optical path of the infra-red energy beam due, for example, to the presence of particulates in the optical path, will not affect the zero balanced condition. To make the detector sensitivity independent of the total amount of infra-red energy entering the detector, a ratio measurement of the infra-red energy measured by each detector 64, 100 can be made.

The detector of this invention also provides an improved and more convenient way to check the calibration of the detector. For example, if a detector is to be used to detect carbon monoxide in stack gas such that concentration of 1000 parts per million (ppm) will provide a full scale reading, the amount of CO in a nitrogen gas sample to simulate 1000 ppm of CO in the stack gas can be calculated. A sample containing the calculated amount of CO in nitrogen is introduced into chamber 74 and an infra-red beam is transmitted into detector 18. The reading on the meter should be full scale and, if not, an appropriate adjustment is made.

Figure 3:
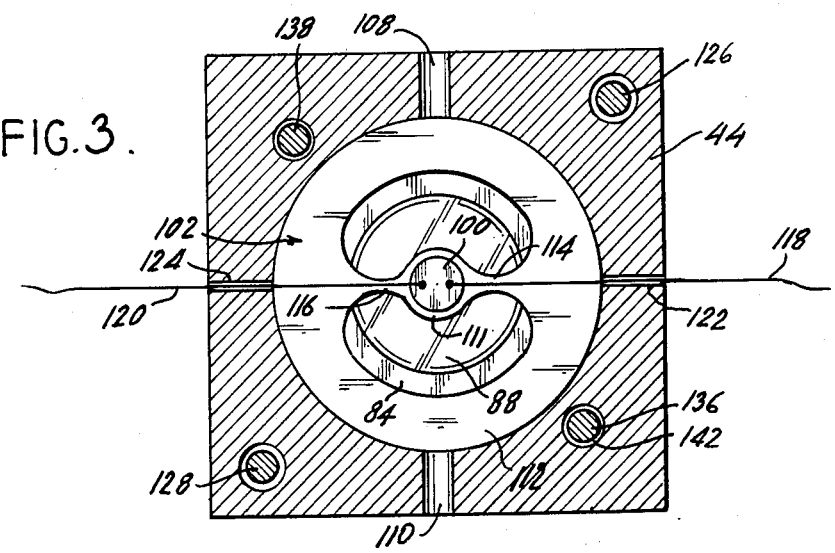
FIG. 3 is a cross-sectional view taken along line 3—3 of FIG. 2 and looking in the direction of the arrows.

Referring now to FIG. 3, second detector carrier 102, which is typical also of first detector carrier 66, includes a central cylindrical body 110 which receives and holds reference infra-red detector 100 and which is joined to outer ring member 112 by thin arms 114, 116. Arms 114, 116 are made as thin as possible so as to provide minimum interference with the beam of infra-red energy as it passes through detector 18. Electrical wire 118, 120 are connected to detector 100, extend along arms 114 and 116, respectively (so as not to interfere with the beam of infra-red energy) and pass through openings 122, 124 in the rear portion 46 of housing 22 for connection to external electrical circuitry, not shown.

Infra-red energy detectors 64 and 100 are preferably mounted in axial alignment, are of the same diameter and have a generally cylindrical configuration. This configuration permits measuring detector 64 to shield reference detector 100 from a portion of the infra-red beam 24 entering detector 18. Thus, only infra-red energy reflected from spherical mirror 90 is incident to reference detector 100. Energy detectors 64 and 100 may be fabricated of any suitable material which provides a signal that responds to the amount of energy imparted to the energy detector by a portion of a beam of infra-red energy. For example, a thermistor which has a resistance which varies in a known manner with temperature as a suitable infra-red energy detector. A thermopile may also be employed as an infra-red energy detector wherein an electric current will be generated that is proportional to the infra-red energy striking the thermopile detector. It should be understood, however, that the invention is not limited to a specific type of infra-red detector.

Figure 4:
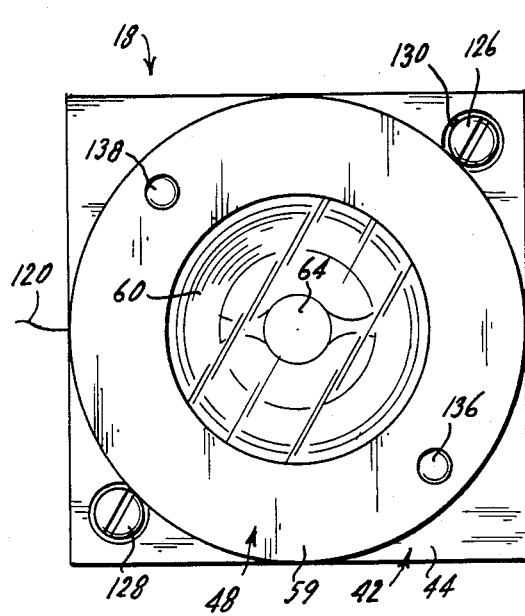
FIG. 4 is a front elevational view of the selective infra-red detector of the invention.
Figure 5:
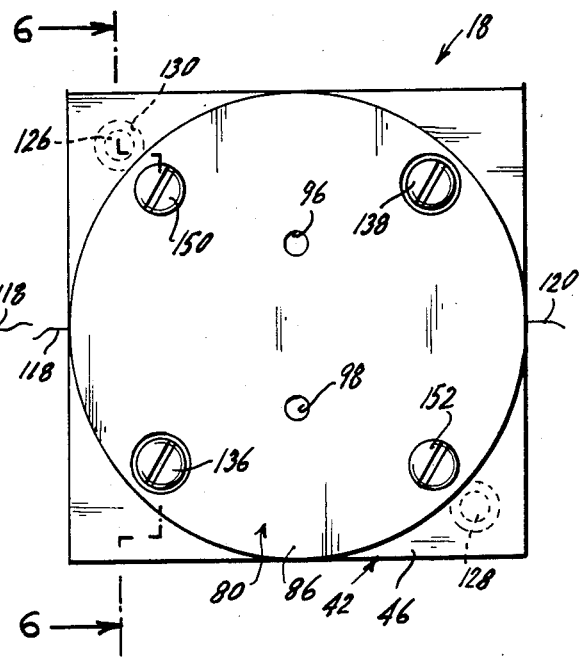
FIG. 5 is a rear elevational view of the selective infra-red detector of the invention.
Figure 6:
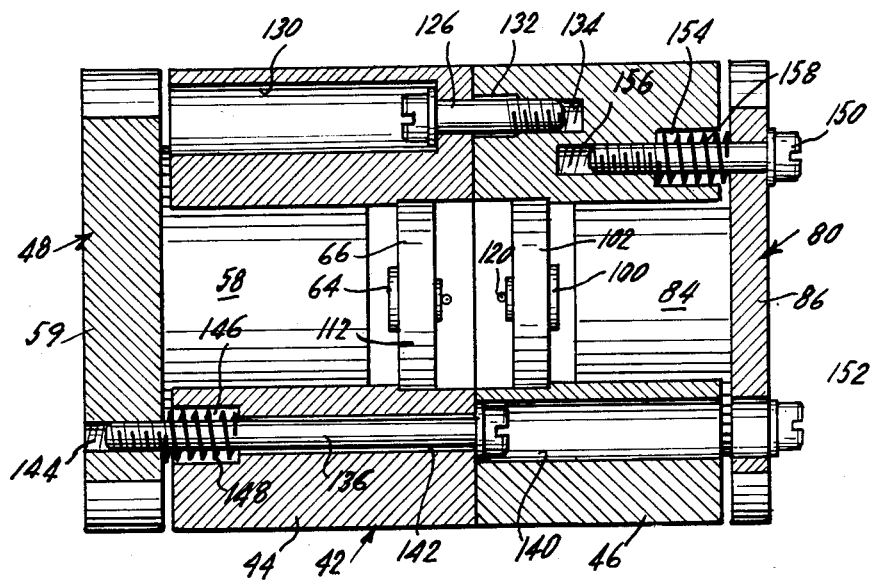
FIG. 6 is a cross-sectional view taken along line 6—6 of FIG. 5 and looking in the direction of the arrow.

Referring to FIGS. 4, 5 and 6, the manner of which the front and rear housing portions 44, 46 are secured together and the manner by which the axial position of the first and second mirror carriers 48, 80 can be adjusted to adjust the position of the first and second focal points 62, 92, will now be described. The front housing portion 44 is secured to the rear housing portion 46 by machine screws 126, 128 which are received within elongated slots (one of which, designated by reference numeral 130, is shown in FIG. 6) pass through bores (one of which, designated by reference numeral 132, is shown in FIG. 6) and engage threaded portions (one of which, designated by reference numeral 134, is shown in FIG. 6) in rear portion 46 of housing 42. Thus, it will be appreciated that the front and rear housing portions 44, 46 can be readily joined together. Axial adjustment of first mirror carrier 48 is affected by machine screws 136, 138 which are received within elongated slots (one of which, designated by reference numeral 140, is shown in FIG. 6) in rear portion 46 of housing 42, passes through bores (one of which, designated by reference numeral 142, is shown in FIG. 6) in the front portion 44 of housing 42 and engages threaded portions (one of which, designated by reference numeral 144, is shown in FIG. 6) in flange 59. Bore 142 has an enlarged portion 146 in which is mounted spring 148 to apply an outwardly directed force on the flange 59 of first mirror carrier 48. Thus, it can be seen that manipulation of machine screw 136 and 138 will cause axial movement of first mirror carrier 48. Similarly, axial adjustment of second mirror carrier 80 is effected by machine screws 150, 152 which pass through enlarged bores (one of which, designated by reference numeral 154, is shown in FIG. 6) in rear portion 46 of housing 42 and engages threaded portions (one of which, designated by reference numeral 156, is shown in FIG. 6) in rear portion 46 of housing 42. A spring 158 is mounted in bore 154 (and another spring, not shown, is mounted in the bore through which machine screw 152 passes) to apply an outward force on flange 86. Thus, manipulation of screws 150, 152 will cause axial movement of second mirror carrier 80. It is significant that axial adjustment of both the first and second mirror carrier takes place through the rear of housing 42 so that there will be no interference with the beam of infra-red energy entering the detector during the adjustment.

While the invention has hereinabove been explained in principle and the preferred construction and mode of operation of the invention has been illustrated and described, it should be understood that modification thereto can be made while still coming within the spirit and scope of the invention which is set forth in the following claims.

What I claim is:

1. A selective gas detecting device for providing an indication of the presence of a selected gas in a gas sample comprising:
   a housing having an inlet opening for receiving a beam of infra-red energy;
   means comprising a parabolic mirror to reflect a first portion of said beam of infra-red energy to a first focal point;
   means comprising a spherical mirror to reflect a second portion of said beam of infra-red energy to a second focal point;
   means to absorb selected spectral wavelengths of said second portion f said beam; and
   first and second energy detectors positioned respectively proximate said first and second focal points to be exposed to infra-red energy and to provide signals which are indicative of the presence of a selected gas in the gas sample.

2. The selective gas detector of claim 1 further including means for moving at least one of said paraboloidal and spherical mirrors to change the position of the first or second focal point, respectively.

3. A selective gas detecting device comprising:
   a housing having a cylindrical bore therein with an inlet opening for receiving a beam of infra-red energy;
   a first mirror carrier mounted for axial movement in said housing;
   a paraboloidal mirror mounted in said first mirror carrier and positioned to reflect a first portion of said beam of infra-red energy to a first focal point;
   a second mirror carrier including a chamber mounted for axial movement in said housing;
   a spherical mirror mounted in said chamber of second mirror carrier and positioned to reflect a second portion of said beam of infra-red energy to a second focal point;
   first and second energy detectors mounted in said housing and positioned between said first and second mirror carriers and proximate said first and second focal points respectively; and
   absorbing means positioned in the chamber of said second mirror carrier to absorb selected spectral wavelengths of said second portion of said beam of infra-red energy.

* * * * *